(12) United States Patent
McBrady et al.

(10) Patent No.: US 8,323,568 B2
(45) Date of Patent: Dec. 4, 2012

(54) MAGNETIC BEAD ASSISTED SAMPLE CONDITIONING SYSTEM

(75) Inventors: Adam Dewey McBrady, Minneapolis, MN (US); Michael Rhodes, Richfield, MN (US); Alex Freeman, Dallas, TX (US)

(73) Assignee: Honeywell International Inc., Morristown, NJ (US)

( * ) Notice: Subject to any disclaimer, the term of this patent is extended or adjusted under 35 U.S.C. 154(b) by 605 days.

(21) Appl. No.: 12/481,737

(22) Filed: Jun. 10, 2009

(65) Prior Publication Data
US 2009/0311804 A1 Dec. 17, 2009

Related U.S. Application Data

(60) Provisional application No. 61/061,393, filed on Jun. 13, 2008.

(51) Int. Cl.
| | |
|---|---|
| G01N 30/96 | (2006.01) |
| G01N 33/48 | (2006.01) |
| G01N 30/02 | (2006.01) |
| G01N 33/543 | (2006.01) |
| B01L 3/00 | (2006.01) |
| C12M 1/34 | (2006.01) |
| B01J 19/12 | (2006.01) |

(52) U.S. Cl. ........... 422/69; 722/68.1; 722/70; 722/500; 722/502; 722/504; 722/505; 722/506; 722/507; 722/186.01; 436/518; 435/287.1; 435/287.2

(58) Field of Classification Search ........................ None
See application file for complete search history.

(56) References Cited

U.S. PATENT DOCUMENTS

| | | | | |
|---|---|---|---|---|
| 2007/0224700 | A1* | 9/2007 | Masters | 436/501 |
| 2007/0292889 | A1* | 12/2007 | Bailey et al. | 435/7.1 |
| 2009/0047297 | A1* | 2/2009 | Kim et al. | 424/184.1 |
| 2009/0053799 | A1* | 2/2009 | Chang-Yen et al. | 435/287.2 |
| 2009/0263794 | A1* | 10/2009 | Nasarabadi | 435/6 |

FOREIGN PATENT DOCUMENTS

WO 2005106023 11/2005

OTHER PUBLICATIONS

Siegel et al., "Cofabrication of Electromagnets and Microfluidic Systems in Poly(dimethylsiloxane)," Angew. Chem. Int. Ed., pp. 6877-6882, 2006.
Siegel et al., "Co-fabrication of Electromagnets and Microfluidic Systems in Poly(dimethylsiloxane),"Angewandte Chemie, Supporting Information, 8 pages, 2006.
Shevkoplyas et al., "The Force Acting on a Superparamagnetic Bead Due to an Applied Magnetic Field," The Royal Society of Chemistry, Lab on a Chip, vol. 7, pp. 1294-1302, 2007.

* cited by examiner

*Primary Examiner* — In Suk Bullock
*Assistant Examiner* — Jennifer Wecker
(74) *Attorney, Agent, or Firm* — Seager Tufte & Wickhem LLC.

(57) ABSTRACT

A magnetic bead assisted sampling system for a fluid sensor. Magnetic beads are dispersed in a sampling volume for collecting the analyte. The beads are packed into a small volume for pre-concentration of the analyte. A solvent may be applied to the beads to elute the analyte from the beads for movement to an analyzer.

7 Claims, 7 Drawing Sheets

MAGNETIC BEAD ASSISTED SAMPLE CONDITIONING SYSTEM

The present application claims the benefit of Provisional Patent Application No. 61/061,393, filed Jun. 13, 2008. Provisional Patent Application No. 61/061,393, filed Jun. 13, 2008, is hereby incorporated by reference.

BACKGROUND

This invention pertains to fluidic analyzers and particularly to microfluidic analyzers. More particularly, the invention pertains to the structure and operation of microfluidic analyzers.

SUMMARY

The invention is a magnetic bead assisted sampling system for a fluid sensor. Magnetic beads are dispersed in a sampling volume for collecting the analyte. The beads are packed into a small volume for pre-concentration of the analyte. A solvent may be applied to the beads to elute the analyte from the beads for movement to an analyzer.

DESCRIPTION

There appears to be many large active research efforts aimed at developing a complete micro-fabricated liquid analysis system. However, many of these systems need highly concentrated samples directly injected into them. As such, they seem limited in their ability to operate on very dilute, low concentration chemical species that exist in many liquid samples. An opportunity exists for the present microscale sample conditioning system capable of pre-concentrating analytes from a large volume liquid sample while maintaining the ability to inject the analytes into a small volume. Moreover, this system should be simple to use and consume relatively little power. A method of sampling large volumes of liquid and concentrating the chemical species therein is needed. The present approach may encompass such a method and device.

The present system may incorporate moving stationary phase methodology for liquid analyte pre-concentration and injection. Some aspects of the present approach may include magnetically active microbeads that have been coated with a sorptive chemical phase. Sorptive-phase coated magnetic microbeads may be dispersed throughout a large sample volume using magnetic fields. The magnetic fields may be adjusted to allow for the beads to circulate throughout the sample's volume. Circulating the sorptive phase coating on the beads may adsorb the chemical analytes in the liquid sample. After a time sufficient to ensure adequate mixing of the liquid volume and the beads, the magnetic fields may be adjusted to bring the beads into a very small volume separate from the sampling volume. At this stage, the beads and any analyte on them may have effectively been pre-concentrated. The preconcentration factor is a ratio of the small volume to the sample volume (assuming 100 percent capture).

Injection may be performed by passing a much stronger liquid solvent over the small volume of microbeads. Whatever volume of strong solvent is needed to remove the analytes from the beads, it may replace the small chamber volume in the pre-concentration factor calculation above.

Figure 1:
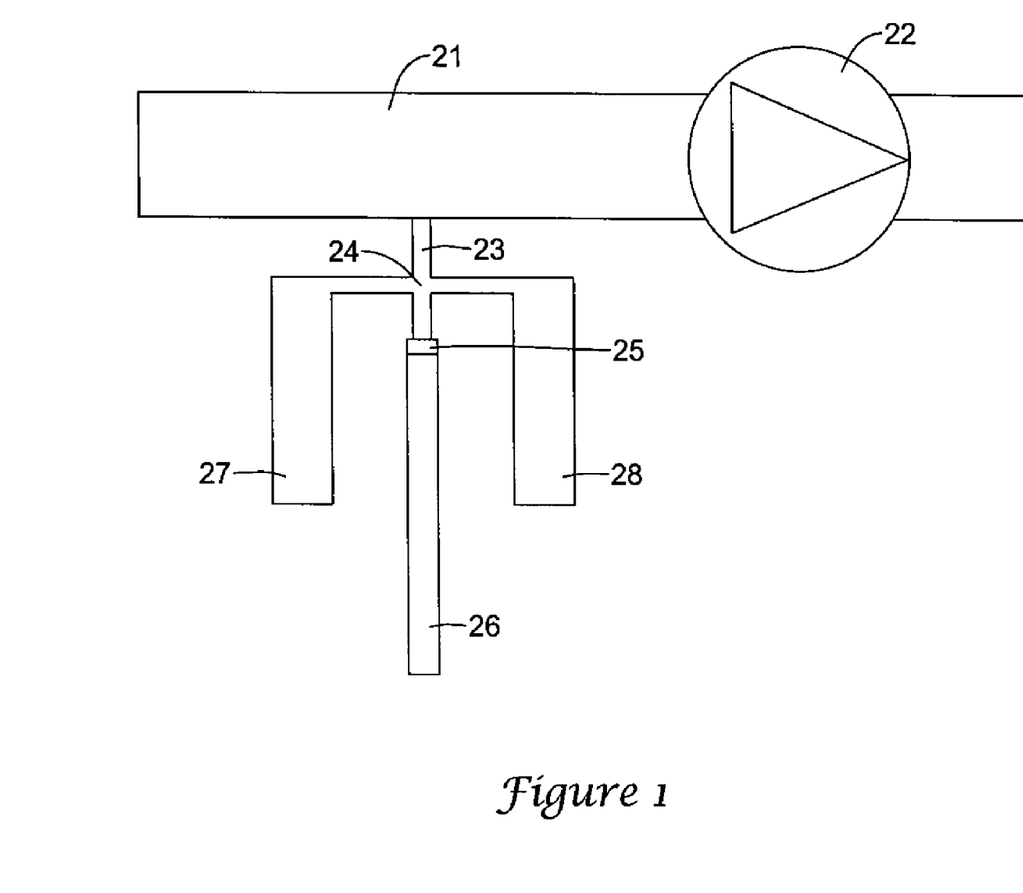
FIG. 1 is a diagram of a device having a sampling reservoir with a pump, a flow manifold between sampling reservoir and a solvent cross volume.

FIG. 1 is a diagram of a device consisting of the following fluidic compartments including a sampling reservoir 21 with a pump 22, a flow manifold 23 between sampling reservoir 21 and a solvent cross volume 24, the solvent cross volume 24 may include a mixing chamber, pre-concentrator 25 having a bead storage volume just before it, an analytical analysis chamber 26, strong and weak solvent reservoirs 27 and 28, respectively, and pumps.

The device may operate by pumping a relatively large volume of sample liquid into a sampling reservoir 21. Sampling reservoir 21 may be designed to minimize the pumping backpressure required to fill it with the liquid sample. After filling the reservoir 21 with liquid sample, a magnetic field may be passed through the sample reservoir 21. Varying the magnetic field may ensure proper mixing and reduce mass transfer times. After a period of time, the magnetic field may be switched to collect the beads and bring them through flow manifold 23 and solvent cross 24 and to pre-concentrator 25.

Once the beads are within pre-concentrator 25, the strong and weak reservoirs 27 and 28, respectively, may be activated such that a dynamically changing solvent mixture with an increasing solvating strength is passed over the beads in pre-concentrator 25. When the solvent mixture is strong enough to desorb the analytes of interest, the analytes may elute off of the beads within a small volume of solvent. Such dynamically changing solvent may produce several sequential injections of analytes off of the pre-concentrator beads in an order of their ability to dissolve in the strong solvent. Once the beads are effectively pre-concentrated and analytes are injected, the analytes may be pumped to the analytical analysis chamber 26. Here desirable analytical or chemical treatment may be effected.

Figure 2:
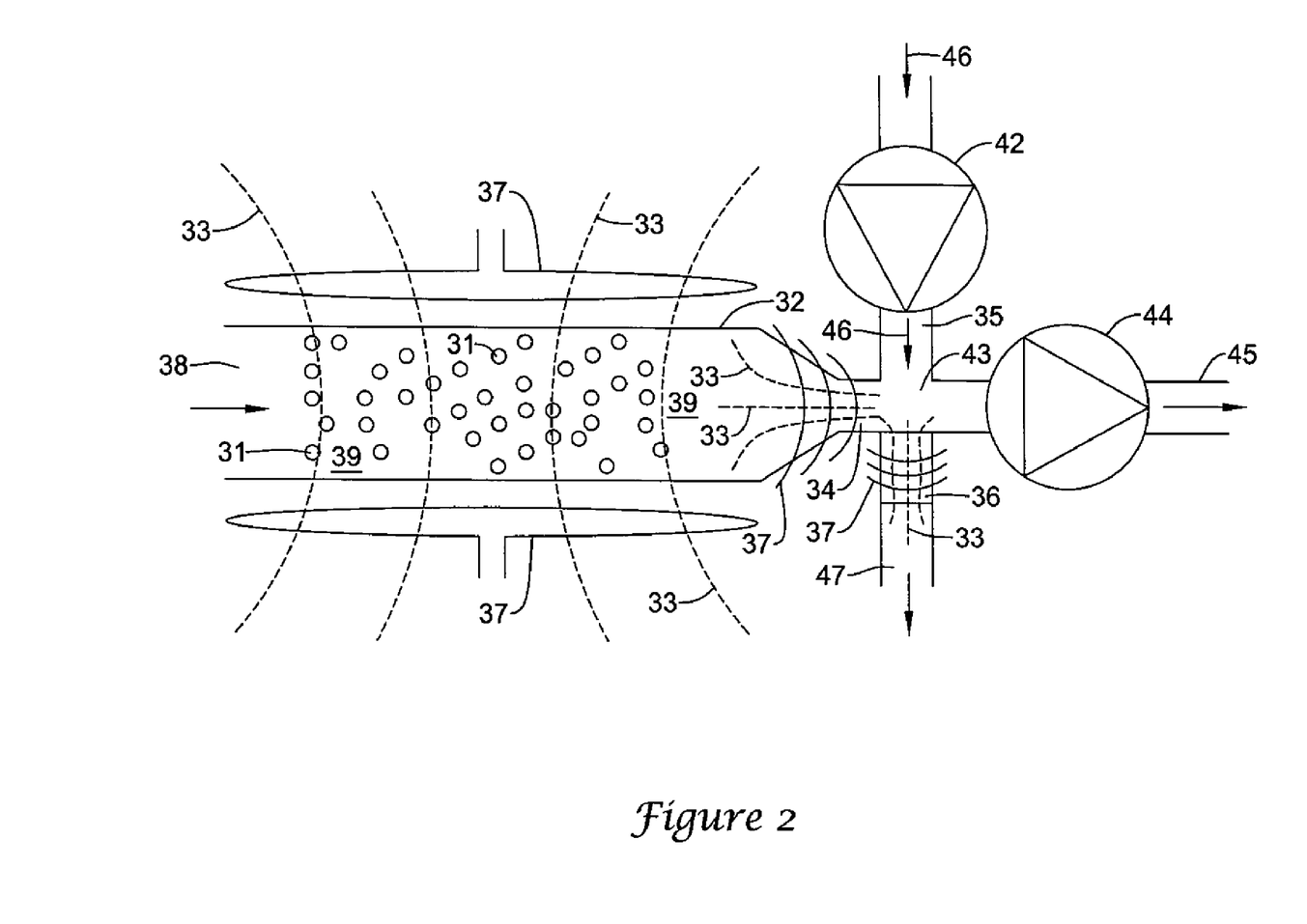
FIG. 2 is a diagram of a fluidic layout of a magnetic bead assisted liquid sampling mechanism.

FIG. 2 is a diagram of a fluidic layout of a magnetic bead assisted liquid sampling mechanism. Upon realization of the mechanism, one may have a ground-breaking pre-concentrator and injector for nearly every liquid based sensor. The mechanism may further relate to micro-LC technology, and indicate that coated magnetic beads 31 can be dispersed throughout a large volume of liquid. Low-level chemical analytes may be pre-concentrated therein. Low volume injections may be achieved via solvent extraction, and be directed back to the sampling position.

There are several items of the system. The first is to disperse magnetic beads 31 throughout a sampling manifold 32 and to maintain their position during the pressure driven sampling flow. The second is to manipulate the external magnetic fields 33 to move the beads 31 through a small volume 34 and into the small volume 36 where the beads can be held for subsequent injection. The third is to move the magnetic beads 31 back to their sampling position after a solvent-based injection at location 36 is performed.

The system may include an approach to manipulate the position of magnetically active absorptive microbeads 31 via external magnetic fields 33 to perform low power sampling, pre-concentration, and injection in a simple and autonomous manner. Other systems for liquid analyte samplers/pre-concentrators might use solid phase micro-extraction (SPME) columns, cartridges, or fibers. Such systems may use polymer absorptive phases coated on the inside of capillaries (SPME columns), coated on tightly packed beads within a larger diameter capillary (SPME cartridges), or coated on inert polymer backbone (SPME fibers).

Some differentiators between other systems and the present system may exist in the mode of operation and the overall size of the devices. Briefly, the operation of many SPME devices may begin with using high backpressures to force sample fluid through the fiber, cartridge or column. During this time the analytes within the sample may adsorb onto the solid phase. SPME columns, fibers and cartridges may be manufactured in as low volume a container as possible (increasing the required back-pressure for sampling and extraction).

Preparing the SPME device for extraction/injection may include a laborious manual or robotic movement of the device inline with a high pressure solvent flow. The high pressure solvent may dissolve the adsorbed analytes and carry them to the rest of the sensor. The high pressures, skilled manpower, and mechanical movements involved in making use of SPME devices may make them of concern to sensors.

The present device may be designed to be the front end for any liquid sensor. The magnetic beads methodology could be electronically controlled in an autonomous manner. When in sampling mode, the magnetic beads 31 may be arranged such that back-pressure is minimized while mass transfer rates are maximized. As such, the dispersed beads should allow reasonably high flow rates at low back pressures while promoting turbulent mixing of the sample fluid. The beads 31 coming through a liquid sample inlet 38 may be in the large sampling volume or manifold 32. A low volume, narrow injection remains possible by moving and compacting all of the magnetic beads after sampling. It is contended that the transition of the magnetic beads from the sampling volume 32 to the injection location 36 be performed electrically and automatically by switching the external magnetic fields 33. The fluidic layout shows a small volume 35 from which the solvent for injection can be delivered, cross 43, and corresponding magnetic fields 33 within the box 36 where the beads 31 gather. Packed within this volume 36, the beads 31, in conjunction with the appropriate mobile phase 46, delivered through volume 35, may serve as an ideal low-volume injector for any subsequent liquid analysis. The analyte may be removed from beads 31, and proceed down path 47 to an analyzer.

Different permeations could include other means of controlling the sampling magnetic field (coil placement, dc or ac), to control magnetic fields 33 within sampling manifold 32. Still other permeations could include use of permanent magnets in conjunction with augmenting/negating electromagnets 37. However, the current needed to produce the fields 33 from the electromagnets could be significant.

Techniques may include production of a sampling manifold 32 with high magnetic permeability material, use of magnetic fields 33 to maintain position of beads 31 during a sampling procedure, moving the position of beads into injection volume 36 via magnetic field 33 manipulation, and recording UV absorbance signal from a sampled, pre-concentrated and injected analyte.

An effective liquid sample conditioning system may have many applications for emerging areas including chemical feed stock quality control, ground water contamination monitoring, and ballast water quality for at sea and near port dumping.

The liquid 39 may carry the beads 31 from the liquid sample inlet 38 into sample chamber of manifold 32. Beads 31 may be directed, not only with a flow of liquid 39, but by the appropriate switching of the three magnetic fields 33 into volume 34 and through the cross chamber 43, into the injection location 36. If the magnetic fields 33 are not sufficient to pack the beads into injection volume 36, a pump 42 may pump a solvent 46 from a reservoir into volume 35 to assist in moving and/or packing the beads 31 from chamber 43 into an injection volume 36. Excess beads may be pumped out of the cross volume 43 by a pump 44 to the sampling waste outlet 45. The beads 31 and analyte may be pre-concentrated in volume 36. With the solvent 46, the analyte is desorbed and eluted off the beads 31 in the injection volume 36 and to a liquid sensor from port 47.

Figure 3:
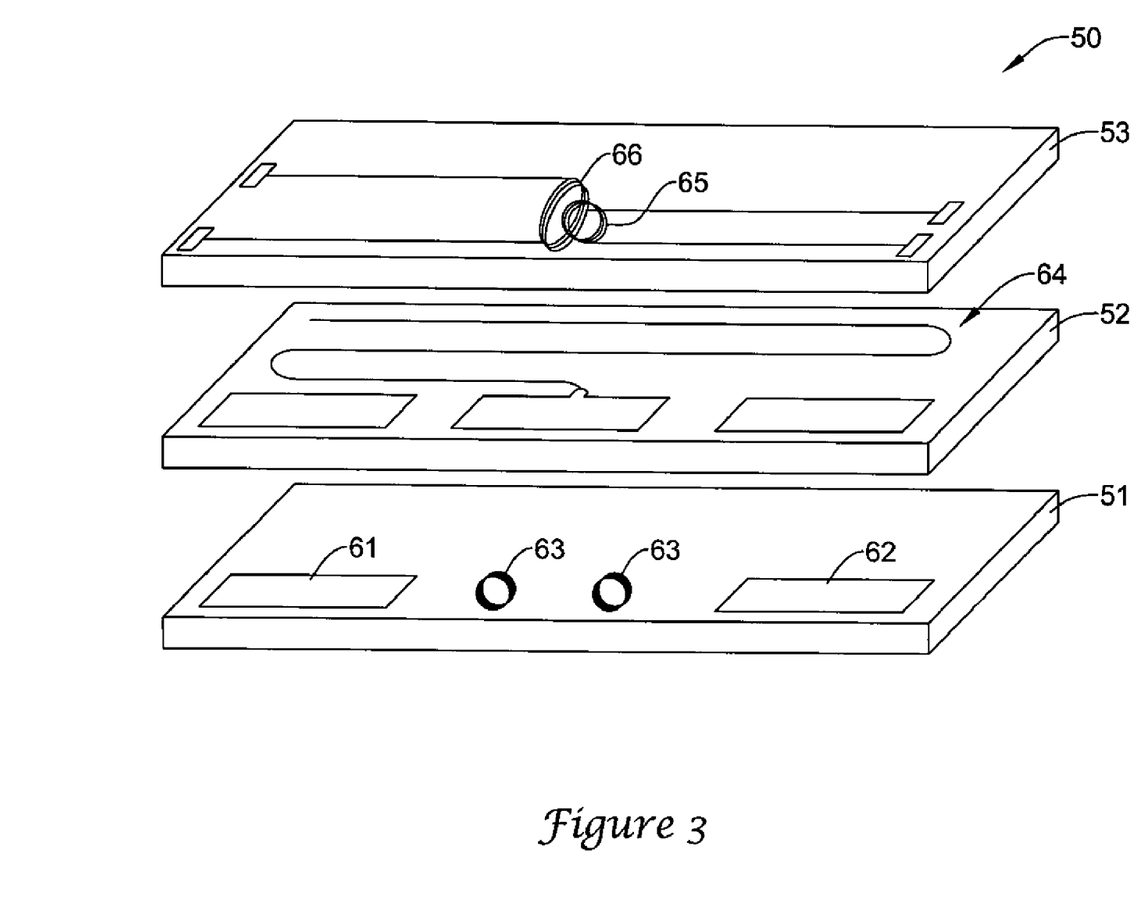
FIG. 3 is a diagram showing an exploded schematic of a magnetically enabled microfluidic analyzer.
Figure 4:
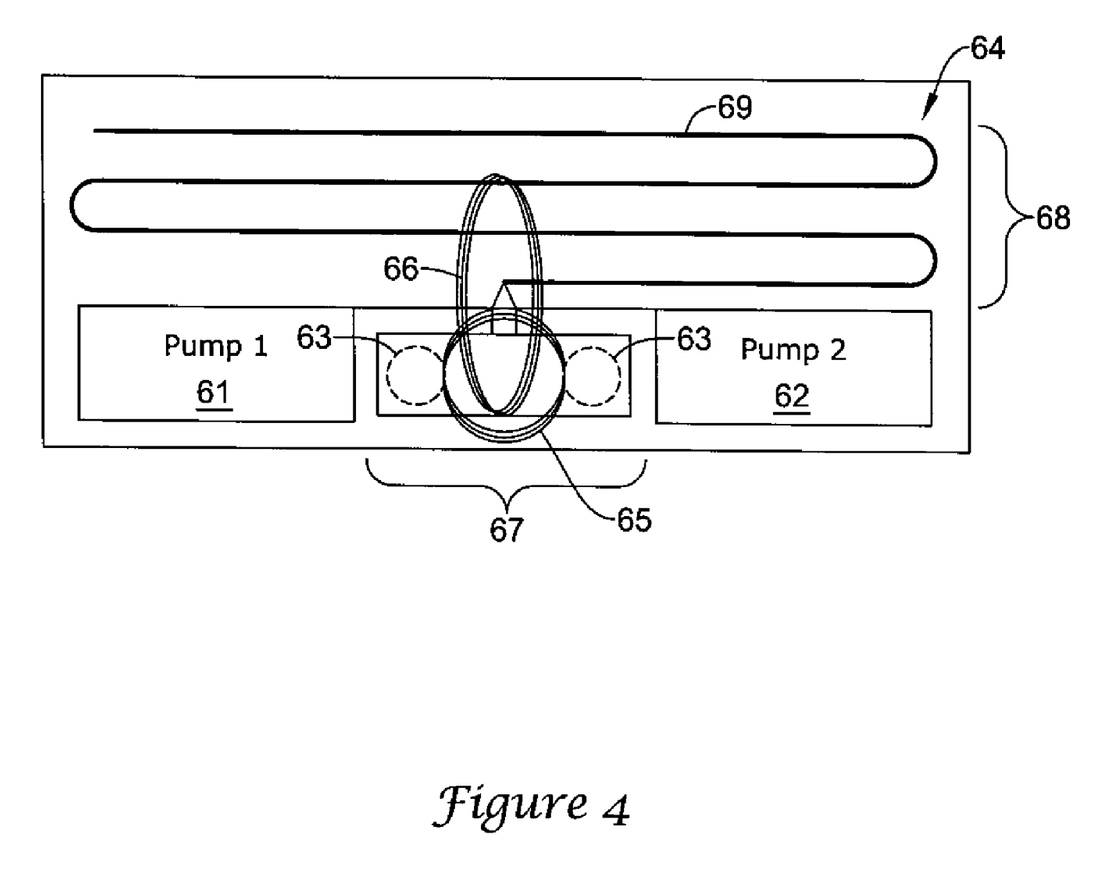
FIG. 4 is a diagram of an overlaid schematic of the layers and of the analyzer.

FIG. 3 is a diagram showing an exploded schematic of a magnetically enabled microfluidic analyzer 50. The analyzer 50 may involve multi-layer MEMS fabrication. There may be a layer 51 which has on-chip pumps 61 and 62 along with appropriate ports 63. Layer 51 may provide on-chip pumping. Layer 52 may contain micro-fluidics 64 including interfacing with pumps 61 and 62, and sampling ports 63. Layer 52 may provide pre-concentration and analysis. Layer 52 may be situated on layer 51. Layer 53 may contain magnets 65 and 66 for bead control. The magnets may be electromagnetic. Layer 53 may be situated on layer 52 resulting in a multi-layer chip analyzer 50. FIG. 4 is a diagram of an overlaid schematic of the layers 51, 52 and 53 of analyzer 50. Portion 67 may provide for sampling, select pre-concentration and injection. Portion 68 may provide for separation and detection. Item 69 may be an analysis channel.

Figure 5:
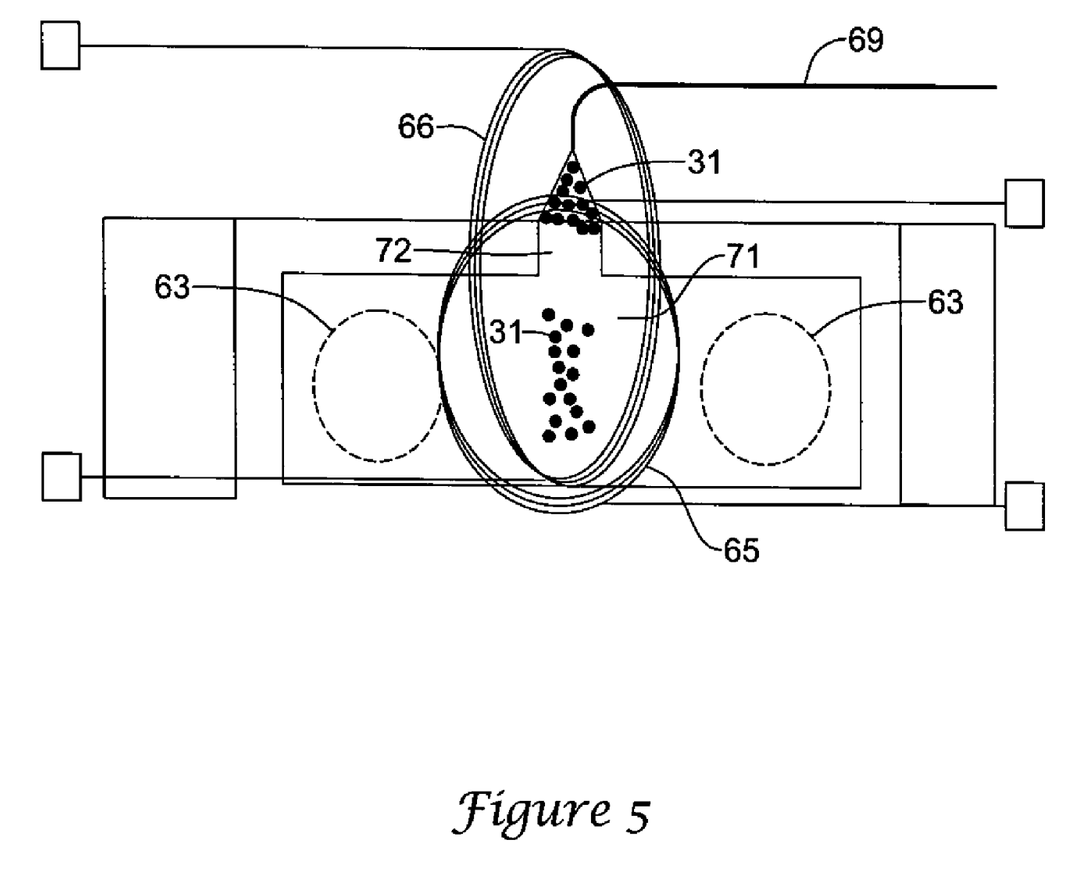
FIG. 5 is a diagram showing bead positions in a sampling volume and in the packed volume leading to an analysis channel.

FIG. 5 shows bead positions in a sampling volume 71 and in the packed volume 72 leading to the analysis channel 69. Samples may enter volume 71 through sampling ports 63. A magnetic force for holding beads 31 in position within volume 71 may be provided for by an electromagnet 65. The moving of beads 31 and being packed into a volume 72 may be effected by an electromagnet 66. The beads 31 may be paramagnetic beads (about 5 or so microns) used to condition samples for various bio-analytical techniques. The on-chip magnetics, i.e., magnets 65 and 66, may permit use of adsorptive paramagnetic beads for sample conditioning for a variety of micro-scale liquid analyzers (CE, IC).

Figure 6:
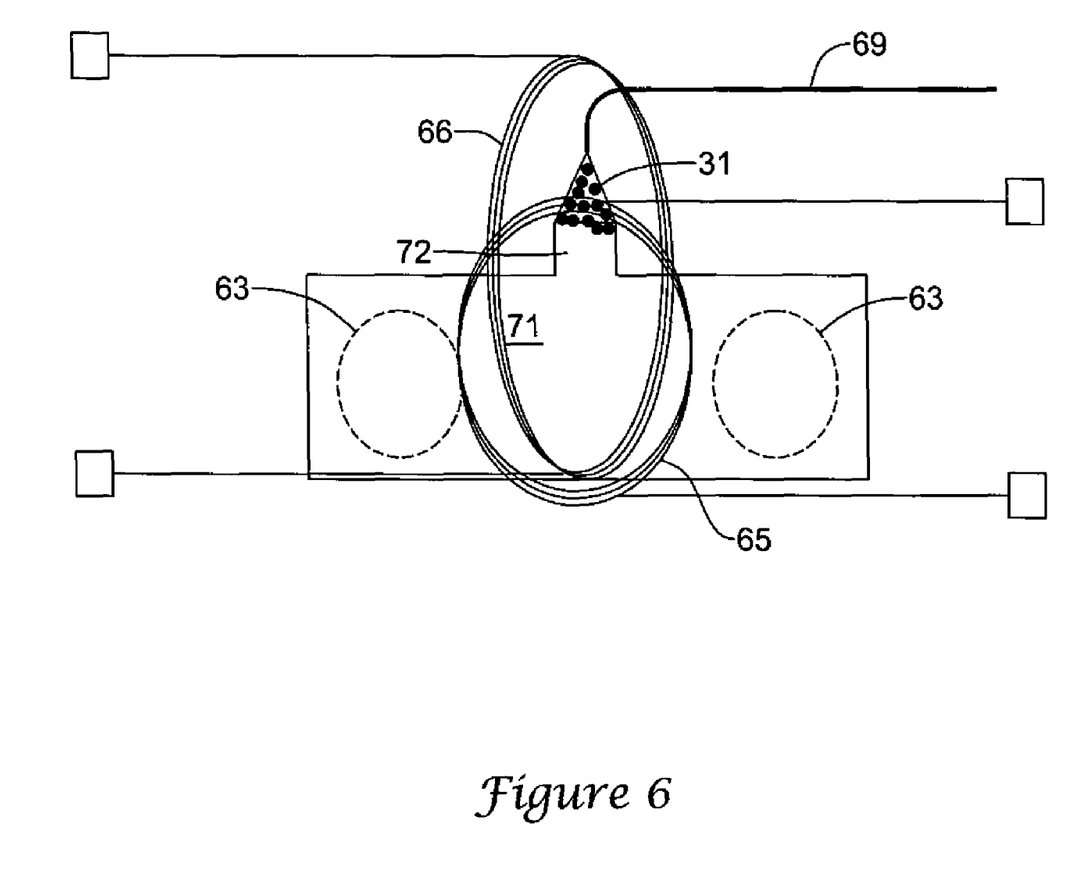
FIG. 6 is a diagram showing how magnetic field manipulation may cause beads to pack into a small volume at a head of analysis channel.

The paramagnetic micron diameter adsorptive beads 31 may be held stationary in the large on-chip sampling volume or chamber 71 during low back pressure high volume sampling using magnet 65. Magnetic field manipulation may cause beads 31 to pack into a small volume 72 at a head of analysis channel 69, as shown in FIG. 6.

Figure 7:
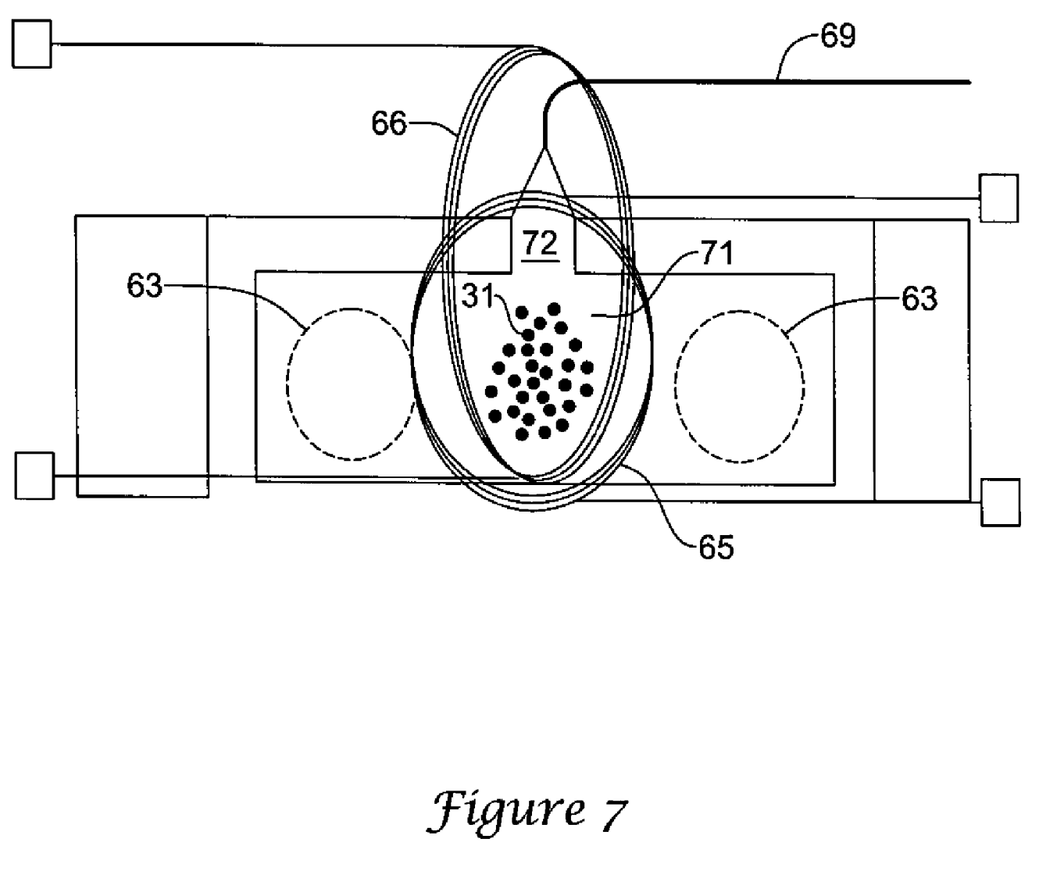
FIG. 7 is a diagram showing a switching of a magnetic field which may distribute clean beads into a sampling reservoir or chamber for an analysis cycle.

Strong on-chip mobile phase pumps 61 and 62 may activate removing adsorbed analytes from the beads 31 and injecting the analytes into the analysis channel 69. Switch a magnetic field of the magnets 65 and 66 may redistribute the now-clean beads into the sampling reservoir or chamber 71 for the next analysis cycle, as shown in FIG. 7.

The present low back-pressure analyzer 50 may be capable of direct sampling of body fluids. There may be selective or universal pre-concentration of analytes of interest from the body fluids. The pre-conditioner needs to be able to condition "dirty" samples" (e.g., urine, blood, sweat) to prevent clogging of the analytical channel 69. The pre-concentrated analytes may be injected onto the on-chip analytical channel (CE, LC, and the like). Pre-concentration gains may be greater than a thousand times for the ratio of sampling volume to injection volume.

The analyzer 50 may be a field-ready bio-analytical microfluidic analyzer for on-site and real-time biochemical warfare or disease exposure identification.

As to magnetic effects of magnets 65 and 66 on beads 31, one may look to pertinent forces. The magnetic force may be proportional to the gradient of the square of the magnetic field as in the following equation.

$$F_B = ((V*X)/\mu_o)\nabla(B^2),$$

where V is the volume of a bead 31, X is magnetic susceptibility and $\mu_o$ is permeability in a vacuum. Stokes drag force due to flow rate may be as indicated in the following equation.

$$F_S = 6\pi\eta r v,$$

where $\eta$ is kinematic viscosity, r is bead radius, v is linear velocity of flow, and laminar flow is assumed. The magnetic force and Stokes drag force need to be equal.

Positions of beads 31 may be maintained against linear flows of about 30 microns per second with an easily achieved ~4 pN force. The magnetic force for holding a bead position may be provided by magnet 65. Sampling large volumes may be enabled by a wide bore sampling channel (high volumes at low linear velocities). The beads 31 may be moved into a packed group in volume 72 by activating magnet 66. The on-chip strong mobile phase pumps 61 and 62 may be activated to elute the pre-concentrated analytes from beads 31 into the analysis channel 69.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A sample conditioning system comprising:
   a sampling chamber having an input and output;
   a plurality of magnet beads;
   a first magnet proximate to the sampling chamber for controlling the magnetic beads in a sample fluid;
   a cross chamber having a first input connected to the output of the sampling chamber, and having a second input, a first output and a second output;
   a solvent source having an output connected to the second input of the cross chamber; and
   a preconcentrator container having an input connected to the first output of the cross chamber; and
   a second magnet proximate the first output of the cross chamber.

2. The system of claim 1, wherein:
   the sampling chamber is for receiving a sample fluid including at least one analyte;
   the magnetic beads are coated with a sorptive chemical phase and provided for dispersion in a sample fluid in the sampling chamber; and
   the sorptive chemical phase on the beads is for adsorbing analytes in the sample fluid.

3. The system of claim 2, wherein the one or more magnets are for dispersing the magnetic beads throughout the sample fluid and then for moving the beads into the cross chamber.

4. The system of claim 3, wherein the one or more magnets are further for moving the beads and any analyte on the beads into a decreasing volume of the preconcentrator container for preconcentration.

5. The system of claim 4, wherein the solvent source is for providing a solvent over the beads to remove the analyte from the beads.

6. The system of claim 1, the sampling chamber comprises a wide bore sampling channel for bringing in one or more samples of fluid in a large volume at low linear velocities.

7. The system of claim 6, further comprising an analyte analysis chamber having an input connected to an output of the preconcentrator container.

\* \* \* \* \*